(12) United States Patent
Hamamatsu et al.

(10) Patent No.: US 7,586,593 B2
(45) Date of Patent: *Sep. 8, 2009

(54) INSPECTION METHOD AND INSPECTION APPARATUS

(75) Inventors: Akira Hamamatsu, Yokohama (JP); Minori Noguchi, Mitsukaido (JP); Hidetoshi Nishiyama, Fujisawa (JP); Yoshimasa Ohshima, Yokohama (JP); Takahiro Jingu, Takasaki (JP); Sachio Uto, Yokohama (JP)

(73) Assignee: Hitachi High-Tech Electronics Engineering Co., Ltd., Tokyo (JP)

( * ) Notice: Subject to any disclaimer, the term of this patent is extended or adjusted under 35 U.S.C. 154(b) by 289 days.

This patent is subject to a terminal disclaimer.

(21) Appl. No.: 11/605,239

(22) Filed: Nov. 29, 2006

(65) Prior Publication Data

US 2007/0070339 A1 Mar. 29, 2007

Related U.S. Application Data

(63) Continuation of application No. 10/722,531, filed on Nov. 28, 2003, now Pat. No. 7,315,363, and a continuation-in-part of application No. 10/724,750, filed on Dec. 2, 2003, now Pat. No. 7,248,352.

(30) Foreign Application Priority Data

Nov. 29, 2002 (JP) ............................. 2002-347134

(51) Int. Cl.
    *G01N 21/00* (2006.01)
(52) U.S. Cl. .................................................. 356/237.1
(58) Field of Classification Search .... 356/237.1–237.5
    See application file for complete search history.

(56) References Cited

U.S. PATENT DOCUMENTS

| 3,658,420 | A |   | 4/1972  | Axelrod         |           |
|-----------|---|---|---------|-----------------|-----------|
| 3,790,280 | A |   | 2/1974  | Heinz et al.    |           |
| RE33,956  | E |   | 6/1992  | Lin et al.      |           |
| 5,274,434 | A | * | 12/1993 | Morioka et al.  | 356/237.4 |
| 5,463,459 | A |   | 10/1995 | Morioka et al.  |           |
| 5,506,676 | A |   | 4/1996  | Hendler et al.  |           |
| 5,629,769 | A | * | 5/1997  | Cookingham et al. | 356/243.1 |
| 5,854,674 | A |   | 12/1998 | Lin             |           |
| 6,031,607 | A |   | 2/2000  | Miyazaki        |           |
| 6,078,386 | A |   | 6/2000  | Tsai et al.     |           |

(Continued)

FOREIGN PATENT DOCUMENTS

JP 59-204820 11/1984

(Continued)

OTHER PUBLICATIONS

Japanese Office Action dated Mar. 27, 2007.

*Primary Examiner*—Roy Punnoose
(74) *Attorney, Agent, or Firm*—Antonelli, Terry, Stout & Kraus, LLP.

(57) ABSTRACT

The present invention provides an inspection apparatus and inspection method. The inspection apparatus includes a stage mechanism for supporting an object under inspection. A spatial filter is provided in the detection optical system to inspect the object. A printer is used to print the results of the spatial filter. The spatial filter can be provided in the form of a Fourier transformed image.

13 Claims, 10 Drawing Sheets

U.S. PATENT DOCUMENTS

| | | |
|---|---|---|
| 6,404,498 B1 | 6/2002 | Maeda et al. |
| 6,411,377 B1 | 6/2002 | Noguchi |
| 6,686,995 B2 | 2/2004 | Wilk et al. |
| 7,315,363 B2 * | 1/2008 | Hamamatsu et al. ..... 356/237.2 |
| 2001/0019411 A1 | 9/2001 | Nara et al. |
| 2002/0154303 A1 | 10/2002 | Maeda et al. |
| 2002/0176074 A1 | 11/2002 | Hasan |

FOREIGN PATENT DOCUMENTS

| | | |
|---|---|---|
| JP | 62-089336 | 4/1987 |
| JP | 1-117024 | 5/1989 |
| JP | 1-250847 | 10/1989 |
| JP | 02-134265 | 5/1990 |
| JP | 5-218163 | 8/1993 |
| JP | 6-258239 | 9/1994 |
| JP | 6-324003 | 11/1994 |
| JP | 8-210989 | 8/1996 |
| JP | 09-043160 | 2/1997 |
| JP | 09-213756 | 8/1997 |
| JP | 09-281324 | 10/1997 |
| JP | 2000-105203 | 4/2000 |

* cited by examiner

CHIP LAYOUT

OR OF FP1, FP2, AND FP3 OBSERVED
FOURIER TRANSFORMED IMAGES

FOURIER TRANSFORM PLANE DIAMETER AND PRINT DOT SIZE

INSPECTION METHOD AND INSPECTION APPARATUS

CROSS REFERENCE TO RELATED APPLICATION

This application is a continuation application of application Ser. No. 10/722,531, filed Nov. 28, 2003 now U.S. Pat. No. 7,315,363, which also relates to continuation-in-part application Ser. No. 10/724,750, filed Dec. 2, 2003 now U.S. Pat. No. 7,248,352, the disclosure of which is hereby incorporated by reference.

BACKGROUND OF THE INVENTION

The present invention relates to an inspection method and inspection apparatus for use in a production line for a semiconductor device, liquid crystal, magnetic head, or other device, and more particularly to a technology for inspecting for foreign matters (particle)/defects.

An example of semiconductor wafer inspection will now be described.

In a conventional semiconductor manufacturing process, any foreign matter existing on a semiconductor substrate (wafer) may cause a wiring insulation failure, short circuit, or other failure. Furthermore, since the semiconductor elements have turned minutely, when a fine foreign matter exists in the semiconductor substrate, this foreign matter causes for instance, insulation failure of capacitor or destruction of gate oxide film or etc. These foreign matters are mixed in the semiconductor substrate by various causes in the various state. As a cause of generating of the foreign matters, what is generated from the movable part of conveyance equipment, what is generated from a human body and the thing by which reaction generation was carried out by process gas within processing equipment, the thing currently mixed in medicine or material used can be considered. A liquid-crystal display device will become what cannot be used, if a foreign matter mixes on a circuit pattern or a certain defect produces a liquid-crystal display device manufacturing process similarly. The same also holds true for a printed circuit board manufacturing process so that foreign matter mixture results in a pattern short circuit or improper connection.

A certain conventional technology for detecting the above-mentioned foreign matters (particles) on a semiconductor substrate, which is disclosed, for instance, by Japanese Patent Laid-open No. 62-89336, illuminates laser light to the semiconductor substrate, detects the light scattered from any foreign matter on the semiconductor substrate, and compares the obtained result against the inspection result of the last inspected semiconductor substrate of the same type to conduct a high-sensitivity, high-reliability, foreign matter/defect inspection while averting a pattern-induced false alarm. Another known technology for inspecting for the above-mentioned foreign matter, which is disclosed, for instance, by Japanese Patent Laid-open No. 5-218163, illuminates coherent light to a wafer, eliminates the light emitted from a repetitive pattern on the wafer with a spatial filter, and enhances non-repetitive foreign matter and defects to achieve detection.

Further, there is a known foreign matter inspection apparatus, which illuminates from a direction having an angle of 45 degrees for major straight line group within a circuit pattern formed on a wafer in order to prevent from entering zero-order diffracted light generated from the major line group into an aperture of an objective lens. As regards the technology incorporated in this foreign matter inspection apparatus (see Japanese Patent Laid-open No. 1-117024), a method for shielding diffracted light generated from non-major straight line group with a spatial filter is disclosed. Furthermore, there are many known conventional technologies concerning an apparatus and method for inspecting for foreign matter and other defects (see Japanese Patent Laid-open No. 1-250847, Japanese Patent Laid-open No. 6-258239, Japanese Patent Laid-open No. 6-324003, Japanese Patent Laid-open No. 8-210989, and Japanese Patent Laid-open No. 8-271437).

SUMMARY OF THE INVENTION

As described in conjunction with the above conventional technologies, in the apparatus employed for inspecting various minute patterns of semiconductor and other devices, although a diffracted light generated from a defect which contain a foreign matter and a diffracted light (pattern noise) generated from a circuit pattern were separated efficiently by space filtering, since a shielding plate with wide width was used from the problem of accuracy mechanical as a spatial filter, the number of diffracted lights generated from the circuit pattern which can shield was restricted.

It is an object of the present invention to provide a technology for performing high-precision spatial filtering to detect foreign matter (foreign particles) and defects at a high sensitivity when a minute circuit pattern is inspected by using an image formed by illuminating white light, single-wavelength light, or laser light.

To achieve the above object according to a first aspect of the present invention, an inspection apparatus comprises an illumination optical system for illuminating light to an object under inspection; a detection optical system for detecting light reflected from the object under inspection and converting the detected light into an electrical signal (an image signal); a spatial filter that is provided in the detection optical system to selectively shield diffracted light coming from each circuit pattern existing on the object under inspection by combining light-shielding points of minute dot state; an arithmetic processing system for processing the electrical signal (the image signal) detected by the detection optical system; and a monitor for observing foreign matter and defects that are presented by a signal processed by the arithmetic processing system.

According to a second aspect of the present invention, an inspection apparatus comprises a stage for moving an object under inspection in a three-dimensional direction; an illumination optical system for illuminating light on the object under inspection, which is mounted on the stage; a detection optical system for detecting light reflected from the object under inspection and converting the detected light into an electrical signal (an image signal); a spatial filter which is provided in the detection optical system and is printed so as to shield the Fourier transformed image of circuit patterns existing on the object under inspection; an arithmetic processing system for processing the electrical signal (the image signal) detected by the detection optical system; and a monitor for observing foreign matter and defects that are presented by a signal processed by the arithmetic processing system. The detection optical system comprises a Fourier transform lens for Fourier transforming the diffracted light coming from the circuit pattern of the object under inspection, and an inverse Fourier transform lens for inverse Fourier transforming the light coming from the spatial filter.

According to a third aspect of the present invention, an inspection method comprises the steps of: illuminating light on an object under inspection; detecting light reflected from said object and converting the detected light into an image signal by a detection optical system; selectively shielding diffracted light coming from a circuit pattern existed on the object in the detection optical system; arithmetically processing the image signal detected by said detection optical system; and observing foreign matters/defects based on a signal derived from said arithmetic processing by a monitor.

According to an inspection method of the present invention, wherein further comprising setting step for setting a plurality of recipes, which differ in intensity of the light to be illuminated on said object, polarized light of illumination light, illumination angle of illumination light, detection visual field size, or detection polarized light setting, and wherein said observing step causes said monitor to display foreign matter and defects on an individual recipe basis.

According to an inspection method of the present invention, wherein said observing step includes assigning step for assigning detection number IDs in accordance with foreign matter/defect position and displaying step for displaying size of the foreign matter/defect assigned said IDs and category indicating a manufacturing process where the foreign matter/defect assigned said IDs is occurred.

According to an inspection method of the present invention, wherein said observing step includes displaying step for displaying foreign matter/defect which is observed by the recipe set by setting step and emphasis indication of the foreign matter/defect to which its attention is paid.

DETAILED DESCRIPTION OF THE PREFERRED EMBODIMENTS

Preferred embodiments of the present invention will now be described with reference to the accompanying drawings.

Figure 1:
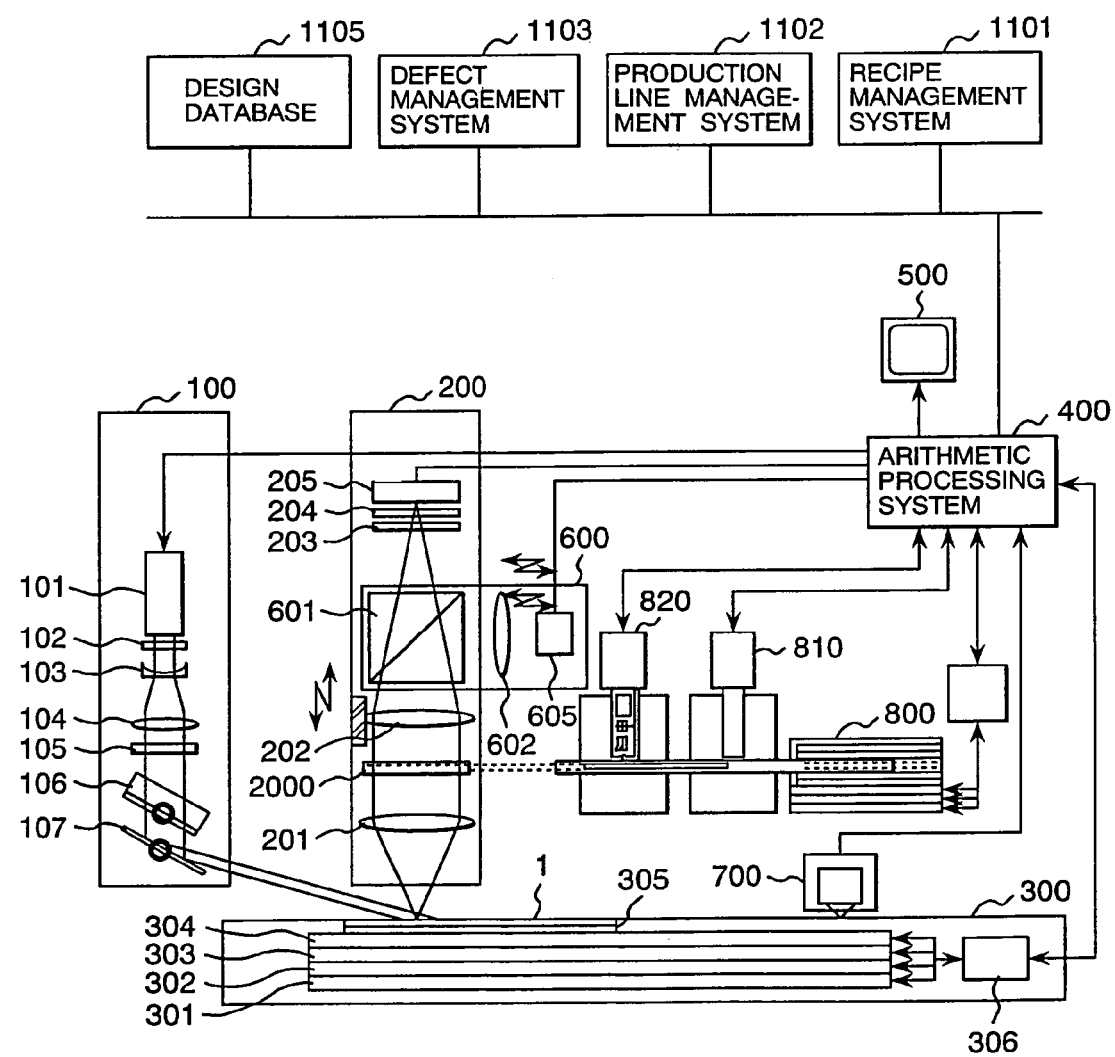
FIG. 1 is a schematic diagram illustrating one embodiment of an inspection apparatus according to the present invention.
Figure 2A:
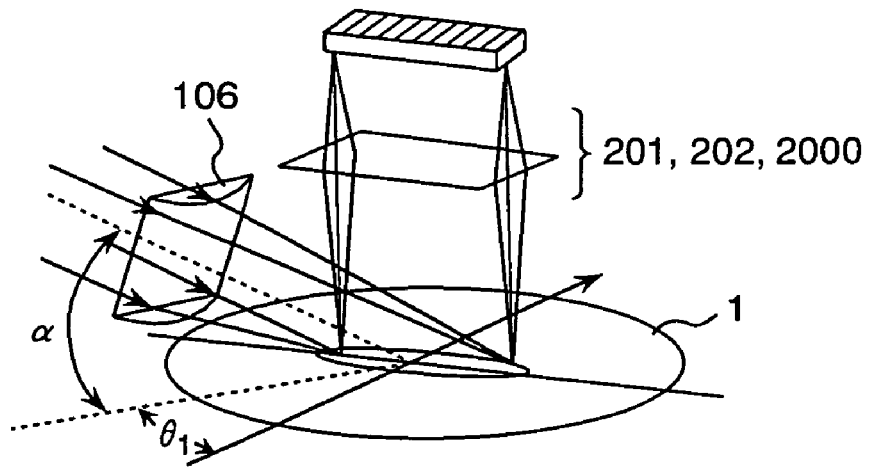
FIGS. 2A and 2B are diagrams illustrating a method for illuminating a wafer surface under inspection with a laser beam.
Figure 2B:
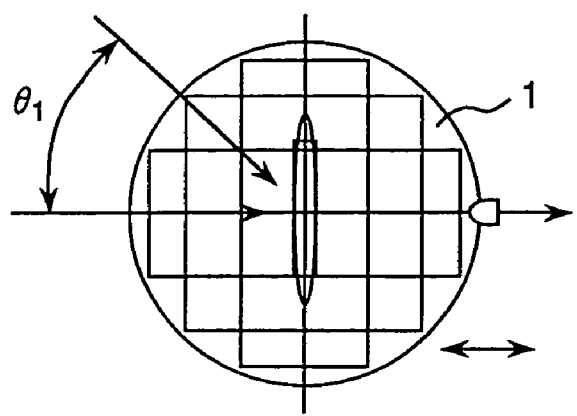

FIG. 1 is a schematic diagram illustrating one embodiment of an inspection apparatus according to the present invention. This inspection apparatus is suitable for inspecting foreign matters and defects. As shown in the figure, the inspection apparatus comprises an illumination system unit 100, a detection optical system unit 200, a stage system 300, an arithmetic processing system 400, a wafer observation unit 500 (monitor 500), a Fourier transform plane observation optical unit 600, a wafer observation optical system 700, a cartridge stocker 800, a filter cleaner 810, a printer 820, and a network-connected server systems 1101-1105, which incorporates various functions. The illumination system 100 comprises a laser oscillator 101, a wavelength plate 102, beam expanders 103, 104 for varying the laser spot size, an aperture diaphragm 105, a cylindrical lens 106, and a mirror 107. The wavelength plate 102 varies the degree of illumination light polarization. The beam expanders 103, 104 vary the illumination size (illumination area). The mirror 107 varies the illumination angle. As shown in FIGS. 2A and 2B, the cylindrical lens 106 is used to illuminate an object under inspection with one side reduced.

FIGS. 2A and 2B are schematic diagrams illustrating a method for illuminating a wafer under inspection with a laser beam. FIG. 2A shows the relationship between the illumination system unit 100 and the detection optical system unit 200. FIG. 2B illustrates a slit-shaped beam spot illuminated on a wafer. As indicated by FIG. 2A, the cylindrical lens 106 is used to reduce the size of an illumination light beam to match a receiving field of a line sensor (CCD or TDI), which is coordinated with the wafer surface for image formation purposes. This also results in efficient use of illumination energy. As shown in FIG. 2B, the cylindrical lens 106 is equipped with an optical system which rotates to provide the same condensation for the front and rear sides of illumination when the light is illuminated from a direction having an angle of θ1 for major straight line group of a circuit pattern formed on the object under inspection. Instead of the cylindrical lens, a cone lens (conical lens) described, for instance, by Japanese Patent Laid-open No. 2000-105203 (equivalent to U.S. patent Ser. No. 09/362,135), may be alternatively used. A slit light beam, which is incident on the wafer surface at an inclination angle of a to the horizontal, bounces off the wafer's surface layer and scatters. A wafer 1 is inspected by running a relative scan over the stage system 300 and detection optical system unit 200. As indicated in FIG. 1, the detection optical system unit 200 mainly comprises a Fourier transform lens (which has a function as an objective lens) 201, an inverse Fourier transform lens (which has a function as an image forming lens) 202, and a sensor 205, and is capable of inserting a spatial filter 2000 into a Fourier transform plane in an optical path. Alternatively, lens 201 may comprise an objective lens and a Fourier transform lens. Lens 202 may alternatively comprise an inverse Fourier transform lens and an image forming lens. In addition, the inverse Fourier transform lens 202 is vertically movable as indicated by an arrow mark so that the magnification can be changed.

Further, an optical path branching device 601 such as a mirror or beam splitter and a Fourier transform plane observation optical unit 600 can be inserted into an optical path. The Fourier transform plane observation optical unit 600 is equipped with a convex lens 602 and a TV camera 605 for observing a pattern in the Fourier transform plane. The convex lens 602 is movable as indicated by an arrow mark so that images of the Fourier transform plane and wafer surface can be formed by the TV camera 605. The signal output from the TV camera 605 enters the arithmetic processing system 400. The detected light, which is derived from the wafer 1, is passed through the inverse Fourier transform lens 202 and optical path branching device 601, polarized by a polarizing plate 203, adjusted by a light intensity adjustment plate 204 to vary its intensity, and incident on the sensor 205. The light is then converted into an electrical signal by the sensor 205, and the resulting electrical signal enters the arithmetic processing system 400. Light diffractions generated from edges of repetitive circuit patterns of the wafer surface are condensed (interfered) into a condensed light pattern (an interference pattern) having regular pitch in the Fourier transform plane. A spatial filter 2000 is set according to the condensed light pattern (the interference pattern) so that the diffracted light generated from the edges of the repetitive patterns do not reach the sensor 205. Meanwhile, it is known that a Fourier image of foreign matter (particle) or defect is not regular and distributes irregularly in the Fourier transform plane. As a result, the light scattered from foreign matter and defects is partly shielded by the spatial filter; however, its greater part reaches the sensor 205. Thus, by setting the spatial filter 2000 according to the condensed light pattern in the Fourier transform plane of the detection optical system unit 200, since the greater part of the scattered light of foreign matter and defects is received by the sensor 205 so that the scattered light (the diffracted light) of the pattern is removed, it becomes possible to detect the foreign matter/defect in high sensitivity by improving a S/N ratio. Since the detection lens of the detection optical system unit 200 is provided with a zoom optical system or an objective lens selector mechanism, it is possible to change the detection magnification. Since a detection pixel size (when they are converted to equivalent values for the wafer surface) becomes small in high magnification mode, it possible to detect the minute foreign matter/defect at a high sensitivity by improving the S/N ratio. However, the inspection speed is low because the detection pixel size are small. On the other hand, by enlarging the detection pixel size in a low magnification mode, inspection speed becomes early and, as a result, it is possible to inspect many wafers within a predetermined period of time. Since a plurality of magnification modes are available, it is possible to use the modes selectively to conduct a low-magnification, high-speed inspection on a product/process to which loose design rules are applied, and a high-magnification, high-sensitivity inspection on a product/process to which severe design rules are applied. The signal acquired by the sensor 205 is subjected to data processing within the arithmetic processing system 400 to output a foreign matter/defect candidate. The result of foreign matter/defect detection is stored as electronic data on a recording medium within the apparatus or in a defect management system 1103 in the network-connected server unit.

A wafer ID and its recipe are entered in a recipe management system 1101 within the server unit. As described later, the recipe contains an illumination light intensity value, illumination polarized light setting, illumination irradiation angle a setting for horizontal surface, illumination irradiation direction $\theta 1$ setting for the layout directions of the chips, detection visual field size, selected spatial filter data, and detection polarized light setting. A production line management system 1102 within the server unit displays data to indicate whether the apparatus is conducting an inspection or on standby and indicate what is flowing on a production line. The defect management system 1103 manages and displays the inspection result of the previous process.

The stage system 300 uses a stage controller 306 to control an X-stage 301, a Y-stage 302, a Z-stage 303, and a $\theta$-stage 304 for the purpose of placing the wafer 1 in a specified position and at a specified height.

The cartridge stocker 800 houses a plurality of cartridges 801a, 801b. The cartridges 801a, 801b have a plurality of filter substrates 802a, 802b that are described later and shown in FIGS. 8A and 8B. After a cartridge 801 is taken out from the cartridge stocker 800, it is cleaned by the cleaner 810, and each of filter substrates 802 is printed the Fourier transformed image of the wafer circuit patterns by the printer 820. The spatial filter 2000 is obtained by printing the Fourier transformed image onto the each of the filter substrates 802. When the foreign matter/defect on each of three kind patterns of the wafer 1 is inspected, the Fourier transformed image of the each three kind pattern is printed onto each three filter substrate. When a spatial filter for inspecting the foreign matter/defect on two kind patterns simultaneously is to be printed, the Fourier transformed images of the two patterns are added together, and the resulting image is printed onto a filter substrate 802 to create a spatial filter. This will be described in detail later.

The foreign matter/defect inspection result, which displays on the monitor 500, will now be described.

Figure 3:
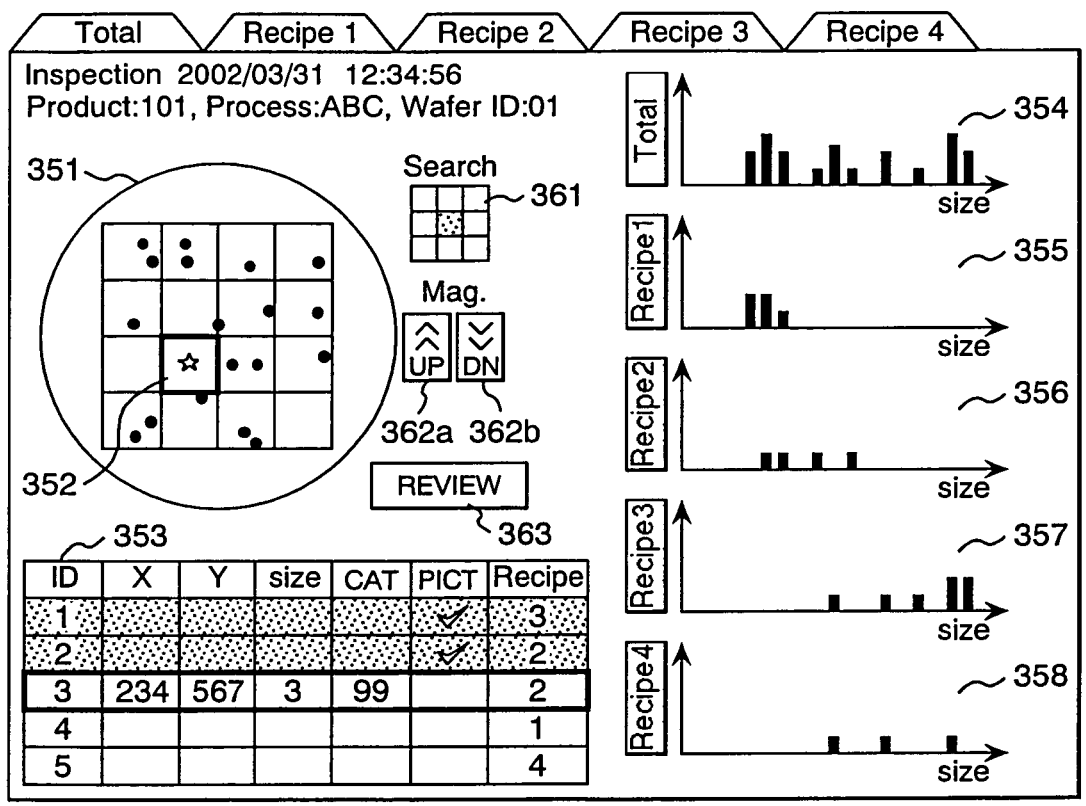
FIG. 3 is a plan view illustrating one embodiment of an inspection result window which displays on a monitor.

FIG. 3 is a plan view illustrating one embodiment of an inspection result window that displays on the monitor. This window shows the result obtained after completion of inspection. The example presented by this figure relates to an inspection that is conducted on a chip on a wafer under more than one set of inspection conditions. Tab names, which appear at the top of the displayed window, represent individual sets of inspection conditions (Recipe 1, Recipe 2, and so on). When a tab name is selected with a mouse or the like, the inspection result obtained under the selected inspection conditions appears. The tab marked "Total" presents the result that is obtained by merging the foreign matter/defect detection results obtained under various inspection conditions in accordance with the wafer's internal coordinate data. The inspection date/time, product type (kind), process, and wafer number are displayed as basic data. Reference numeral 351 denotes a wafer map that roughly indicates positions of the foreign matters/defects on the wafer. On the wafer map 351, an emphasis indication of the foreign matter/defect 352 to which its attention is paid now is given. Moreover, an emphasis indication also of the tip including the defect is given similarly. Further, the foreign matter/defect information is displayed in tabular form 353. This tabular form 353 indicates a detection number (ID) assigned to foreign matter/defect, the X- and Y-coordinates for indicating the foreign matter/defect position, the foreign matter/defect size (SIZE), a foreign matter/defect category (CAT), a flag (PICT) for indicating whether a photo is taken, and the inspection condition set (Recipe) used for detection. The foreign matter/defect category field indicates whether the foreign matter/defect was generated upon plasma emission or attached during transfer or film formation or due to chemical reaction. The contents of the tabular form can be sorted again in ascending or descending order on an individual object basis to suit the purpose. Further, the foreign matter/defects reviewed are visually distinguished from those which are not reviewed. Furthermore, the foreign matter/defect 352 to which its attention is paid now can also be indicated by emphasis with a thick outline etc. In addition, detected foreign matter/defects are classified by size and displayed in histogram form. Histogram 354 depicts "Total" information. Recipes 1 to 4 are displayed in histograms 355 to 358. Reference numeral 361 denotes a search button for switching to the on-screen information about another chip. Pressing a desired display area changes the chip to be displayed. Reference numeral 362a denotes a button for increasing the display magnification, and reference numeral 362b denotes a button for decreasing the display magnification. Reference numeral 363 denotes a REVIEW button for changing the displayed window. This button is used, for instance, to switch from the window shown in FIG. 3 to the one shown in FIG. 4, which will be described below.

Figure 4:
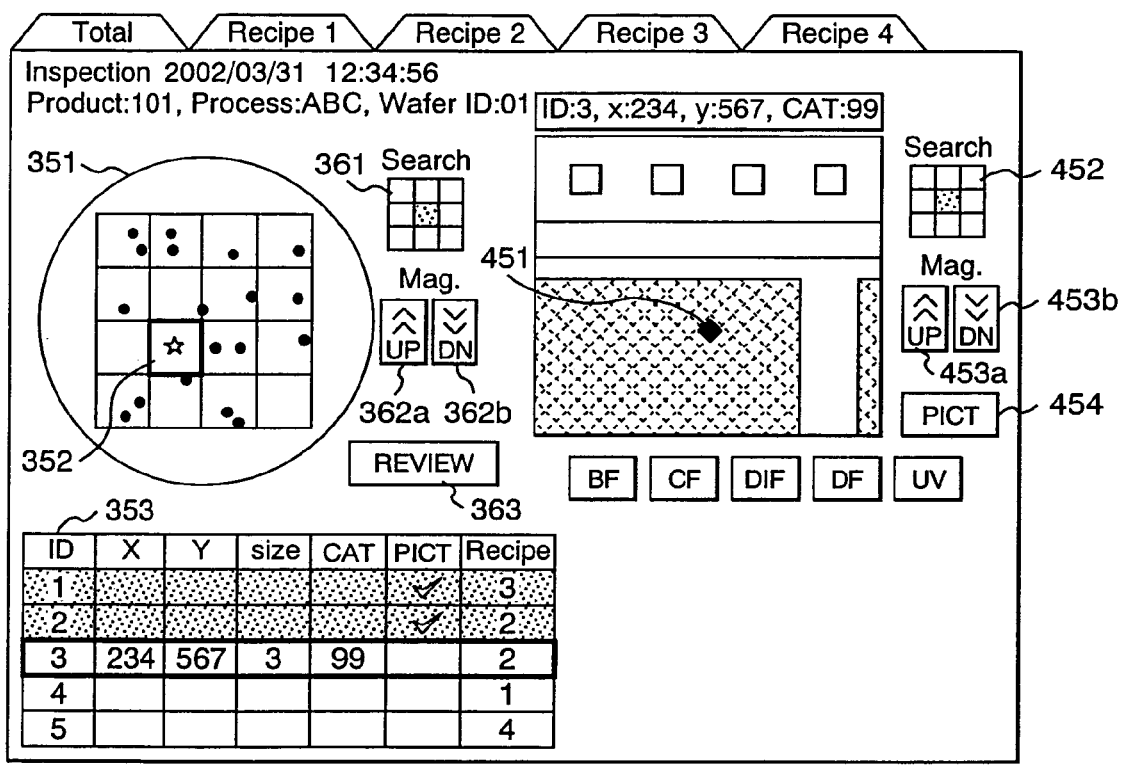
FIG. 4 is a plan view illustrating another embodiment of an inspection result window which displays on a monitor.

FIG. 4 is a plan view illustrating another embodiment of an inspection result window that appears on a monitor. It is an example of a foreign matter/defect review window. The window displays a foreign matter/defect review image 451 of a specified chip. As a review optical system, a confocal optical system (CF), a differential interference optical system (DIF), a dark field optical system (DF), and an ultraviolet or other short-wavelength optics (UV) are selectable in addition to a regular bright field optical system (BF). Further, a search button 452 is furnished to facilitate a foreign matter/defect search. This button makes it possible to move directly to the upper, lower, left-hand, right-hand, upper right, lower right, upper left, or lower left visual field. The magnification of the detection optical system 200 can be changed with magnification change buttons 453a, 453b. Further, pressing the PICT button 454 picks up the image of the currently reviewed visual field.

Figure 5:
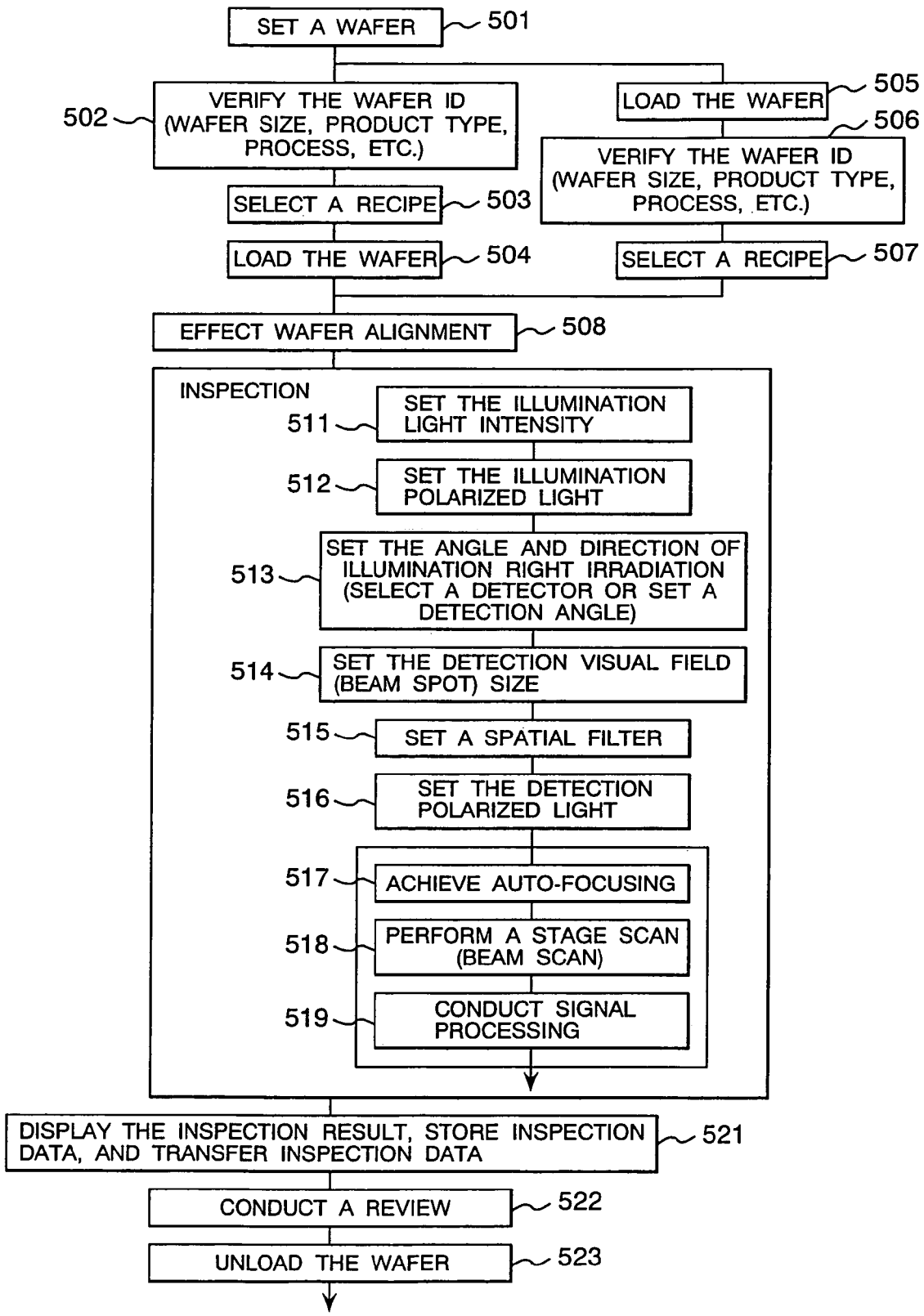
FIG. 5 is a flowchart illustrating a foreign matter/defect inspection process that is performed in accordance with one embodiment of the present invention.

FIG. 5 is a flowchart illustrating a foreign matter/defect inspection process that is performed in accordance with one embodiment of the present invention. In step 501 in this figure, a wafer cassette (SMIF, etc.) in which a plurality of wafers are mounted is set automatically or manually. In step 501, the ID of a wafer is confirmed. With a wafer ID, it is possible to identify the wafer size, product type, and process. The wafer ID may be entered or selected by an inspection operator or received from a database included, for instance, in the production line management system. In step 503, a recipe (inspection conditions) is selected automatically or manually in accordance with the wafer ID. In step 504, the wafer is loaded onto a stage within the apparatus.

As indicated by a branch shown in the figure, if a wafer inscribed with a wafer ID is loaded in step 505, the wafer ID is recognized during loading as indicated in step 506, and then a recipe selection can be made in step 507.

After the wafer is loaded onto a stage within the apparatus, the stage block 300 moves the X-, Y-, Z- and θ-stages in step 508 to effect wafer alignment, and then proceeds to conduct an inspection.

In an inspection sequence, the intensity of the illumination light to be irradiated on the wafer is set in step 511 according to a recipe selected from a plurality of prepared recipes. In step 512, the polarized light of the illumination light to be irradiated on the wafer is set. In step 513, the inclined angle α and direction θ of illumination light irradiation for the wafer (rotation angle θ around an axis perpendicular to the wafer) is set. In step 514, the size of a detection visual field (beam spot) is set. In step 515, a spatial filter is set. In step 516, either the p-polarized light or s-polarized light is selected as the polarized light to be detected.

The actual inspection operation then starts. While the wafer surface layer is auto-focused in step 517, a stage scan is performed as indicated in step 518. Step 519 is performed simultaneously with auto-focusing and stage scanning to conduct signal processing for foreign matter/defect extraction. Upon completion of inspection, step 521 is performed to display the result of inspection on the monitor, store inspection data, and transfer inspection data to the server and the like. Step 522 is then performed to conduct a foreign matter/defect review as needed. In step 523, the wafer is unloaded to terminate the inspection sequence.

To achieve high inspection throughput, an image formation, laser light scattering type inspection apparatus indicated in the present embodiment may use an inspection visual field as wide as several micrometers or more. In a wide-field inspection, different patterns may be irradiated by illuminating the entire inspection area or wider area (by subjecting it to laser radiation). A method for forming a spatial filter in such a situation will now be described with reference to FIGS. 6A to 6C.

Figure 6A:
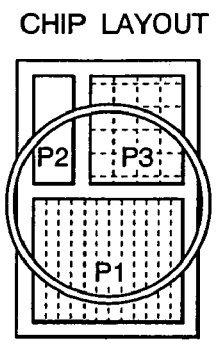
FIG. 6A shows two or more kinds of circuit patterns P1, P2 and P3 which are formed on the wafer and the illumination area illuminated light on the wafer.
Figure 6B:
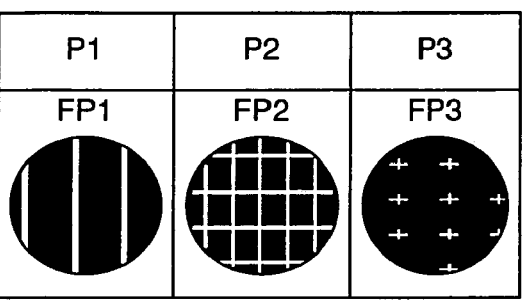
FIG. 6B shows the diffracted light patterns which are the Fourier transform images FP1, FP2, and FP3 of each circuit pattern in the case of detecting the foreign matter/defect on two or more kinds of circuit patterns.
Figure 6C:
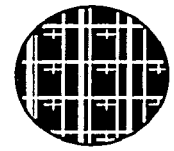
FIG. 6C shows a logical OR of the Fourier transform images FP1, FP2, and FP3 observed.

FIGS. 6A, 6B, and 6C are wafer and diffracted light pattern diagrams that illustrate Fourier transformed images used to detect foreign matter/defect on a plurality of patterns. FIG. 6A shows patterns and illumination area on a wafer. FIG. 6B shows diffracted light patterns that can be derived from patterns on a wafer. FIG. 6C shows an OR pattern of diffracted light patterns. As indicated by the illumination area 651 in FIG. 6A, the Fourier transform plane contains a plurality of diffracted light patterns FP1, FP2, FP3 if a plurality of patterns P1, P2, P3, which differ in the pattern pitch, are illuminated within a chip. If the diffracted light patterns FP1, FP2, FP3 are inspected in this state with a synthesized spatial filter, diffracted light patterns FP1, FP2, and FP3 for patterns P1, P2, and P3 can be simultaneously shielded so as to provide an advantage of making it possible to reduce the pattern signal. On the other hand, the light scattered from a defect is considerably shielded when a plurality of diffracted light patterns are shielded. This creates a disadvantage of causing the signal S from a defect to decrease.

When, for instance, a specific memory area M1 is to be inspected at a high sensitivity, it is necessary to perform spatial filter setup by acquiring a Fourier transformed image in a state of that diffracted light patterns other than that of memory area M1 are shielded.

The following three methods are conceivable:

The first method is to insert an illumination range limiting aperture diaphragm in the optical path of the illumination optical system. The second method is to limit the illumination range by varying the beam magnification with a movable beam expander. The third method is to reduce the NA of the convex lens 602 within the Fourier transform plane observation optical unit 600. All these methods reduce the visual field.

The method for reducing the NA of the convex lens 602 of the Fourier transform plane observation optical unit 600 will now be described in detail. In the Fourier transform lens 201, the angle of incidence on the Fourier transform plane corresponds to the distance (radius) from the visual field center on an object surface. More specifically, when the NA of the convex lens 602 is reduced, it is possible to acquire only the light having a small angle of incidence on the Fourier transform plane, that is, to acquire only the diffracted light arising out of an area whose distance from the visual field center is within a limited range on the object surface.

When any of the above method is chosen, it is possible to acquire only the diffracted light from a specific area (that is, to reduce the visual field). This makes that it is possible to set a light-shielding pattern that is appropriate for a diffraction pattern generated from a specific area. As the result, a specific memory area M1 can be inspected at a high sensitivity.

When only the diffracted light generated from the specific area can be acquired as described above, foreign matter and defects existed on pattern P1 of the wafer can be inspected by using a spatial filter that is obtained by printing diffracted light pattern FP1 as a Fourier transformed image. Further, foreign matter and defects existed on a patterns P2 or P3 of the wafer can be similarly inspected by using a each spatial filter on which a Fourier transformed image FP2 or FP3 is formed.

A spatial filter printing unit will now be described with reference to FIG. 7.

Figure 7:
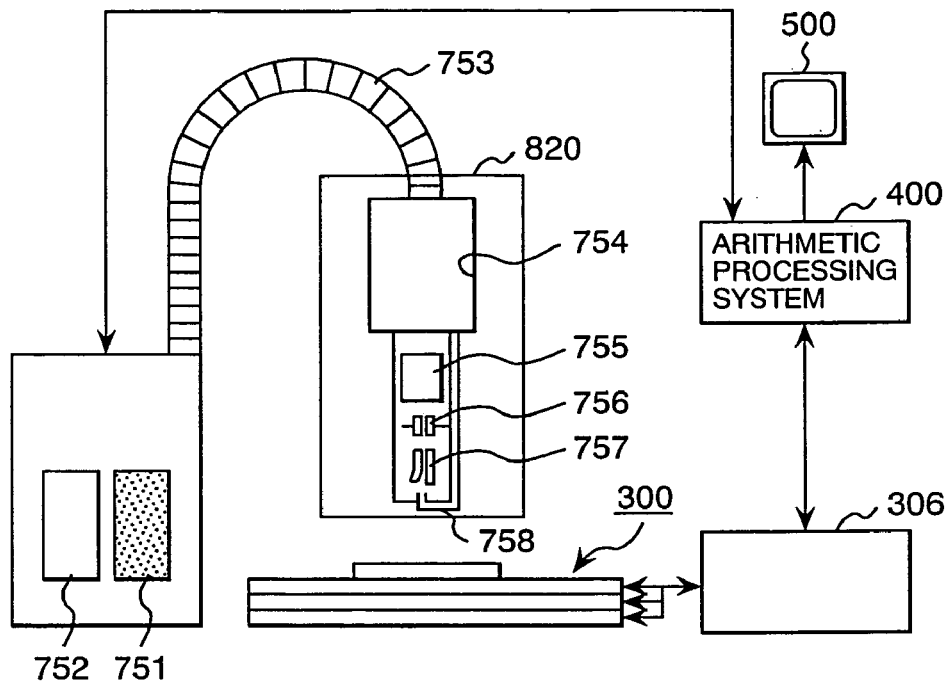
FIG. 7 is a schematic configuration diagram illustrating one embodiment of a spatial filter printing unit according to the present invention.

FIG. 7 is a schematic configuration diagram illustrating one embodiment of a spatial filter printing unit according to the present invention. The data for spatial filter printing is transmitted to a printer that is connected to the arithmetic processing system 400. The stage 300, which holds a glass plate, and the printer, such as an inkjet printer 820, are synchronously operated by the arithmetic processing system 400 to make a print. The inkjet printer is equipped with a mechanism that averts or clears an ink-induced clog. For example, a methyl ethyl ketone or other cleaning liquid 752 that dissolves ink 751 is provided to clean an ink path. Alternatively, a clogged ink discharge function, which increases the inkjet pressure, may be furnished. The ink 751 passes through a pipe 753 and stays in an ink holder 754. The ink 751 is grained by a piezoelectric element 755, electrically charged by an electrode 756, and deflected by a deflector 757. A Fourier transformed image set by the arithmetic processing system 400 is then printed onto a spatial filter substrate 802. Excess ink, which has not been used for printing, is collected in a gutter 758.

A cartridge equipped with a cartridge filter substrate for spatial filter printing will now be described with reference to FIGS. 8A and 8B.

Figure 8A:
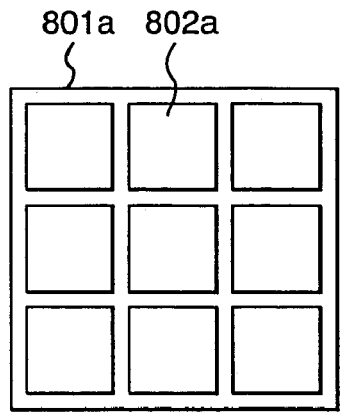
FIGS. 8A and 8B are plan views illustrating one embodiment of a spatial filter cartridge according to the present invention.
Figure 8B:
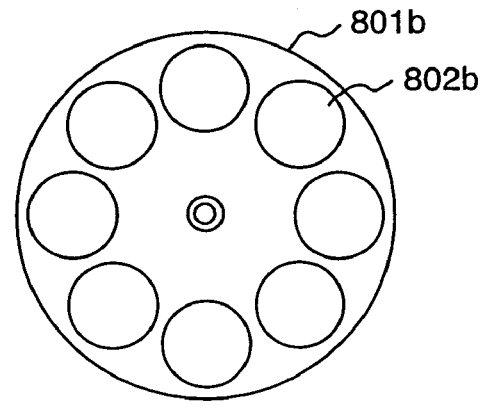

FIGS. 8A and 8B are plan views illustrating one embodiment of a spatial filter cartridge according to the present invention. FIG. 8A illustrates a first embodiment whereas FIG. 8B illustrates a second embodiment. The figure illustrating the first embodiment shows nine square spatial filter substrates 802a, which are mounted on a square cartridge 801a. The figure illustrating the second embodiment shows nine circular spatial filter substrates 802b, which are mounted on a circular cartridge 801b.

As shown in the figures, the spatial filter glass plates can be managed with the cartridge 801a/801b so as to support many product types and processes. In an example in which nine spatial filter substrates 802a/802b, which are glass plates, are mounted on a single cartridge 801a/801b, it is possible to support for four to nine patterns on a process of a logic product (nine inspection areas). Therefore, the Fourier transformed images can be printed, for instance, for the patterns FP1, FP2 and FP3 and a combination pattern (a OR pattern) as shown in FIGS. 6A to 6C. It is also possible to support for three patterns (pattern of memory circuit, pattern of peripheral circuit, and merged pattern of memory and peripheral circuits) on a process of a memory product.

Figure 9A:
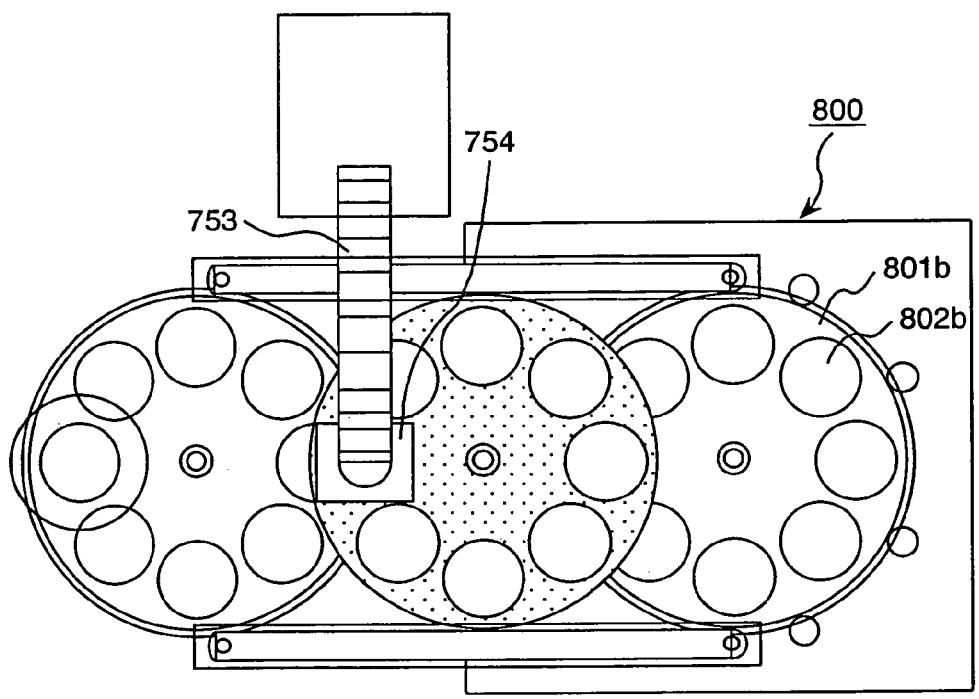
FIGS. 9A and 9B are a top view and a plan view, respectively, which illustrate one embodiment of a cartridge storage/pullout mechanism.
Figure 9B:
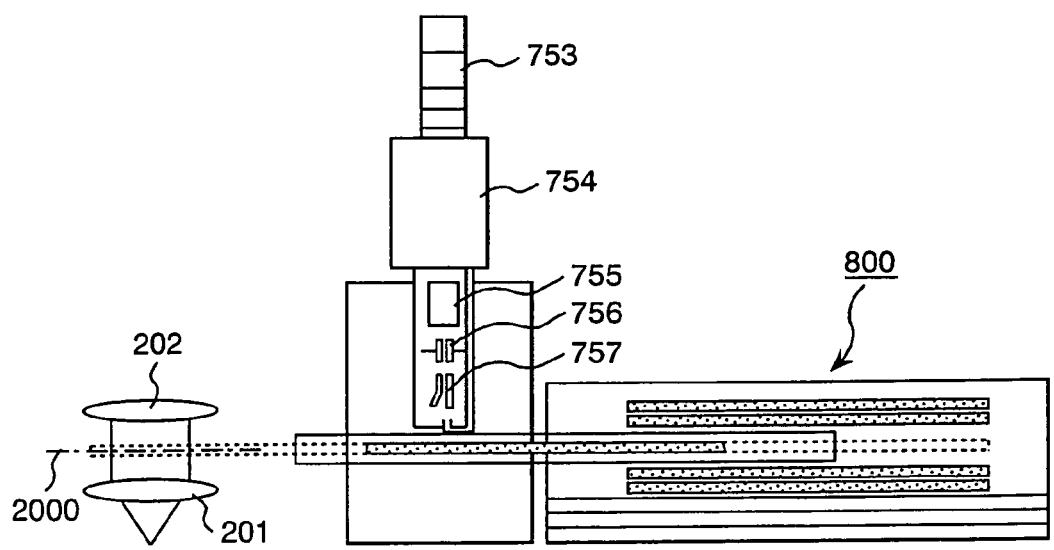

FIGS. 9A and 9B are a top view and a plan view, respectively, which illustrate one embodiment of a cartridge storage/pullout mechanism. FIG. 9A is a top view, whereas FIG. 9B is a plan view. Elements identical with those described earlier are assigned the same reference numerals as their counterparts and will not be described again. The cartridge stocker 800 houses a plurality of cartridges. One of such cartridges is pulled out of the cartridge stocker 800. The printer 820 prints the Fourier transformed image of a specified pattern on the wafer onto a first spatial filter substrate, which is placed in a specified location for printing. Next, a second spatial filter substrate moves to a specified location for printing, and the Fourier transformed image of a specified pattern on the wafer is printed onto the second spatial filter substrate.

The accuracy of spatial filter printing by an inkjet printer will now be described with reference to FIG. 10.

Figure 10:
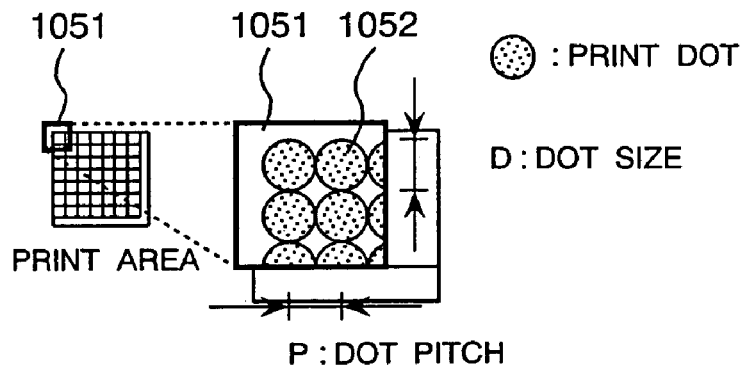
FIG. 10 is a plan view of a printed matter printed with an inkjet printer.

FIG. 10 is a plan view of a print that is printed by an inkjet printer. When a print area 1051 is printed as shown in the figure, a gap arises between print dots 1051 as indicated in the enlarged view of the print area, thereby degrading the spatial filter performance. The reason is that the relationship between the normal dot size and dot pitch is preset so that D (dot size)≦P (dot pitch). To avoid this problem, it is necessary to provide interpolation so as to fill the gap between the print dots.

Methods for print dot interpolation will now be described with reference to FIG. 11.

Figure 11:
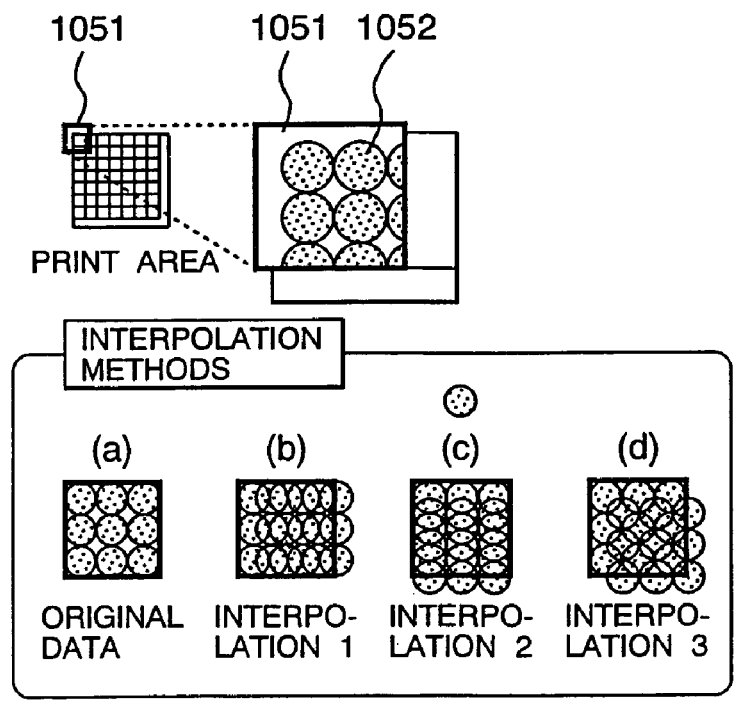
FIG. 11 is a schematic diagram illustrating interpolation methods of print dots.

FIG. 11 is a schematic diagram illustrating print dot interpolation methods. When method (a) is used, a print is made with print data, but no interpolation is provided with interpolation data. Therefore, a gap arises between print dots 1052. On the other hand, method (b), which is a first interpolation method, provides interpolation by printing interpolation dots 1053 horizontally according to interpolation data with a view toward filling the gaps between the print dots 1052. Method (c), which is a second interpolation method, provides interpolation by printing interpolation dots 1053 vertically. Method (d), which is a third interpolation method, provides print dot interpolation by printing interpolation dots 1053 obliquely.

Figure 12:
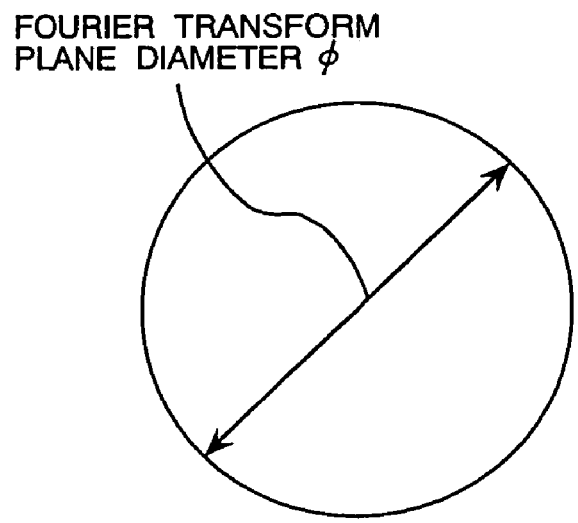
FIG. 12 is a schematic diagram illustrating the relationship between the size of a Fourier transform plane and the size of a print dot.
Figure 12:
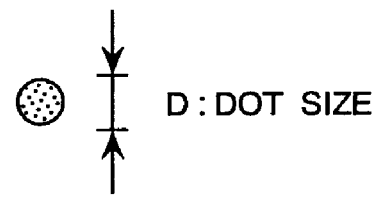

FIG. 12 is a schematic diagram illustrating the relationship between the size of a Fourier transform plane and the size of a print dot. If $D \leq 1/50 \times \phi$ is satisfied according to the experiment, where D is the print dot size and $\phi$ is the Fourier transform plane diameter, a fine print can be made to form a spatial filter that does not permit leakage of the diffracted light.

As described above, the present invention detects foreign matter and defects with high accuracy and at a high sensitivity by using a spatial filter on which a Fourier transformed image of a pattern on a wafer is printed.

What is claimed is:

1. An inspection apparatus comprising:
    a stage mechanism which supports an inspection object;
    a spatial filter for inspecting the object; and
    a printer which prints the spatial filter on a cartridge.

2. The inspection apparatus according to claim 1, wherein said stage mechanism provides a stage which mounts the inspection object and moves the inspection object in a three-dimensional direction.

3. The inspection apparatus according to claim 1, wherein said spatial filter is a printed Fourier transformed image of a circuit pattern of the inspection object.

4. The inspection apparatus according to claim 1, further comprising the cartridge equipped with a plurality of substrates for forming the spatial filter and a cleaner which cleans the substrates of the cartridge, and therein said printer prints a Fourier transformed image of a circuit pattern of the inspection object to the substrates of the cartridge.

5. The inspection apparatus according to claim 3, further comprising a monitor which can observe an inspection result.

6. The inspection apparatus according to claim 4, further comprising a monitor which can observe an inspection result.

7. The inspection apparatus according to claim 1, wherein said printer is a dot printer, wherein D<P where D is dot size and P is print pitch, and wherein interpolation is provided for a gap between dots.

8. The inspection apparatus according to claim 7,
    wherein $D < 1/50 \times \phi$ if a diameter of Fourier transform plane within a circuit pattern of said inspection object is $\phi$.

9. The inspection apparatus according to claim 7, wherein said printer comprises a stage which holds a glass plate and an inklet printer which is equipped with a mechanism that clears an ink-induced clog.

10. The inspection apparatus according to claim 7, wherein said printer includes a collecting unit which collects excess ink that has not been used for printing.

11. An inspection method comprising the steps of:
   printing a Fourier transformed image of a pattern of an inspection object to a cartridge;
   providing the printed cartridge as a spatial filter at a desired position of an inspection apparatus; and
   inspecting the inspection object by using the spatial filter.

12. The inspection method according to claim 11, wherein the step of printing includes a step of printing to the substrate by adding (combining) a Fourier transformed image of each of a plurality of patterns of the inspection object.

13. The inspection method according to claim 11, wherein the step of printing includes a step of printing an interpolation data corresponding to gaps between dots.

* * * * *

UNITED STATES PATENT AND TRADEMARK OFFICE
CERTIFICATE OF CORRECTION

PATENT NO. : 7,586,593 B2  Page 1 of 1
APPLICATION NO. : 11/605239
DATED : September 8, 2009
INVENTOR(S) : Hamamatsu et al.

It is certified that error appears in the above-identified patent and that said Letters Patent is hereby corrected as shown below:

Item (73) Assignee, please amend as follows:

Hitachi High-Technologies Corporation (JP)

Signed and Sealed this

Twenty-sixth Day of January, 2010

David J. Kappos
*Director of the United States Patent and Trademark Office*